(12) United States Patent
Schwartz

(10) Patent No.: US 7,714,710 B2
(45) Date of Patent: May 11, 2010

(54) METHOD AND SYSTEM FOR TRACKING EQUIPMENT EMPLOYING RF-ID TECHNOLOGY

(75) Inventor: Gary Allen Schwartz, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 465 days.

(21) Appl. No.: 11/577,014

(22) PCT Filed: Sep. 22, 2005

(86) PCT No.: PCT/IB2005/053141

§ 371 (c)(1),
(2), (4) Date: Apr. 11, 2007

(87) PCT Pub. No.: WO2006/040696

PCT Pub. Date: Apr. 20, 2006

(65) Prior Publication Data

US 2008/0094208 A1    Apr. 24, 2008

Related U.S. Application Data

(60) Provisional application No. 60/618,013, filed on Oct. 12, 2004.

(51) Int. Cl.
*G08B 1/08* (2006.01)
*G08B 5/22* (2006.01)

(52) U.S. Cl. .............. 340/539.13; 340/539.21; 340/825.49

(58) Field of Classification Search ... 340/568.1–572.9, 340/539.21, 825.49
See application file for complete search history.

(56) References Cited

U.S. PATENT DOCUMENTS 6,901,304 B2 * 5/2005 Swan et al. ............... 700/115

(Continued)

FOREIGN PATENT DOCUMENTS

EP    1316814 A1    4/2003

OTHER PUBLICATIONS

"Fundamental Operating Principles" Klaus Finkenzeller; RFID Handbook; Fundamentals and Applications in Contactless Smart Cards and identifications, John Wiley & Sons, Ltd., 2003, 30 pages.

(Continued)

*Primary Examiner*—Jennifer Mehmood

(57) ABSTRACT

Disclosed is a method and system for determining the location of at least one of a plurality of uniquely-identified transducers within one of a plurality of known areas (210-270). The method comprises the steps of receiving information from at least one sensor selected from a plurality of first (211, 212, 216) and second sensors (218, 228, 238), wherein the first sensors (211, 212, 216) are distributed within the plurality of known areas, and the second sensors are located between adjacent ones of the plurality of known areas (220, 240), the information including at least a transducer-unique identification, associating the received information based on the transducer identification, and determining the location based on the information received by at least one of the first sensors. In one aspect the information is a signal strength. In another aspect of the invention, the location may be determined based on information received by a plurality of the first sensors. In another aspect of the invention, the transition of the transducers from one area to an adjacent area may be determined and such transition stored in a database.

31 Claims, 3 Drawing Sheets

U.S. PATENT DOCUMENTS 7,142,120 B2 * 11/2006 Charych et al. .......... 340/572.4
7,242,306 B2 * 7/2007 Wildman et al. ......... 340/573.1
2002/0145526 A1 * 10/2002 Friedman et al. ......... 340/573.5
2004/0171935 A1 9/2004 Van Creveld

OTHER PUBLICATIONS

"Digital Imaging and Communications in Medicine (DICOM)" Part 1: Introduction and Overview, National Electrical Manufactures Association; 2003, 20 pages.

* cited by examiner

METHOD AND SYSTEM FOR TRACKING EQUIPMENT EMPLOYING RF-ID TECHNOLOGY

CROSS REFERENCE TO RELATED APPLICATION

This application claims the benefit of U.S. Provisional Application No. 60/618,013, filed on Oct. 12, 2004.

This invention is related to the field of electronic tracking and, more specifically, to a method and system for tracking equipment using RF-ID technology.

As computer and electronic technologies continue to be incorporated into business and commercial settings, organizations must continue to track existing, and newer, equipment as they are added to the inventory. Hence, inventory control and management has become an important aspect of many businesses. This is particularly true when there is a limited amount of equipment and the equipment must be shared between parties or offices and it is in-use, located in a different office or unusable due to repair or maintenance. In another aspect, as equipment becomes smaller and lighter, there is a likelihood that it may be taken or stolen and, hence, lost permanently.

In many hospitals, for example, medical equipment is shared between different offices, laboratories or diagnostic rooms as they are needed. Most equipment utilizes one or more ultrasonic transducers that perform specific functions. Further, the transducers may be interchangeable with other equipment. For example, portable diagnostic studies are common in ultrasound, with imaging systems and their associated transducers being moved through the hospital to the patients' bedside. However, time is often lost in locating equipment, devices and/or the transducers when needed. One method of saving time in locating devices is to provide significant duplication of the equipment or transducers. However, this is very expensive and only exacerbates the problem as equipment is added to the existing inventory and the added equipment also must be accounted for and controlled. Furthermore, the cost of the transducers is relatively high as each transducer can represent between 5 and 20% of the equipment's cost. With regard to specialty applications, the transducers may be shared among several systems, across several exam rooms or clinics, and the determination of their location may become a critical issue.

Hence, there is a need in the industry for a method and system for managing and controlling inventory in which equipment can be quickly located and utilized more efficiently.

A method and system for determining the location of uniquely-identified transducers within a plurality of known areas are disclosed. The method comprises the steps of receiving information from at least one of a plurality of first and second sensors, wherein the first sensors are distributed within a plurality of known areas and the second sensors are located between the adjacent ones of the plurality of known areas, the information including at least a transducer identification, associating the received information based on the transducer identification and determining the location of the transducer, and a corresponding device, based on the information received by at least one of the sensors. One aspect of the information is a signal strength. In another aspect of the invention, the location may be determined based on the information received by a plurality of the first sensors. In another aspect of the invention, a transition of the transducers from one area to an adjacent area may be determined and such transition stored in a database.

Figure 1:
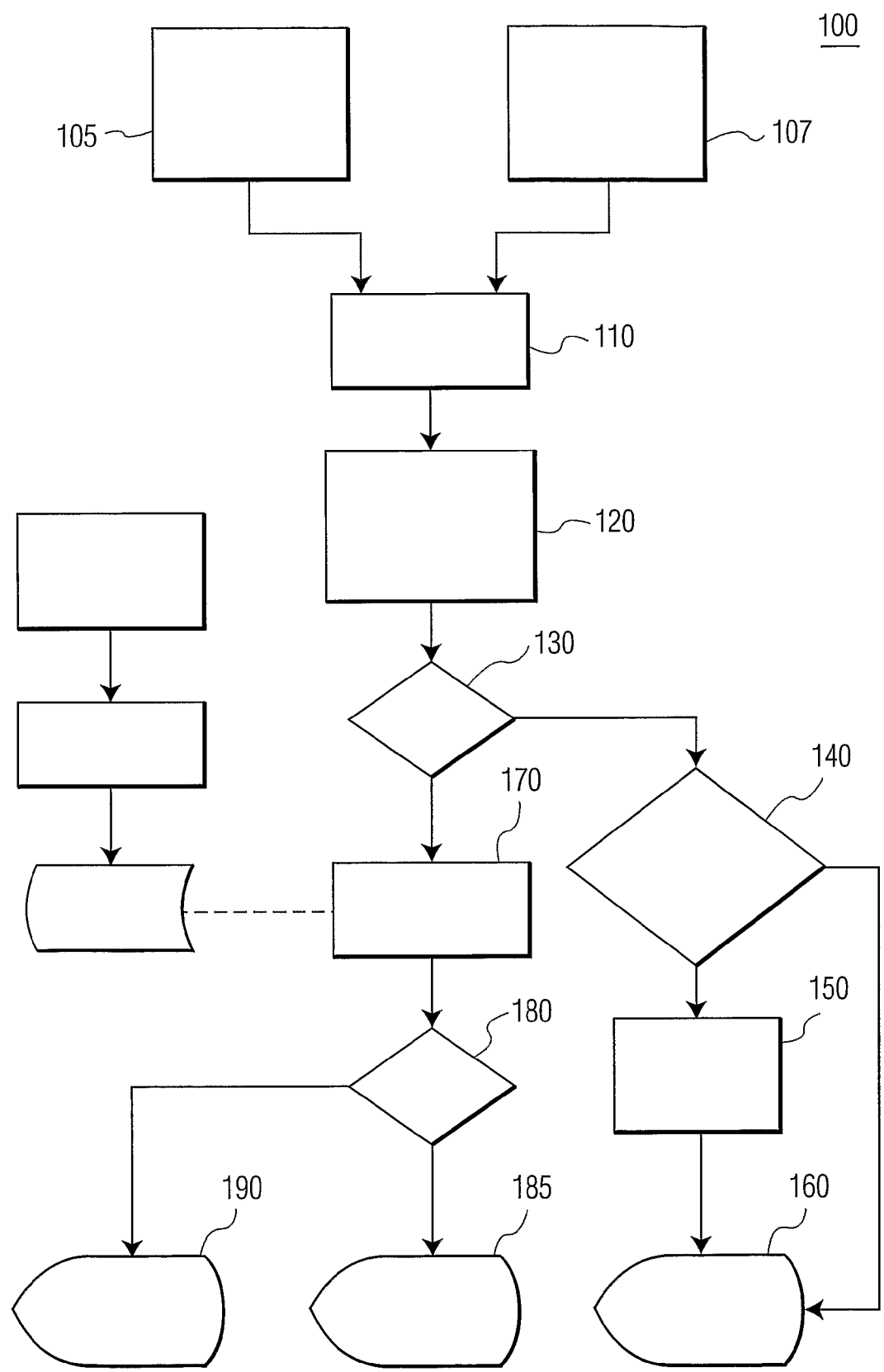
FIG. 1 illustrates a flow chart of a process for managing equipment/inventory in accordance with the principles of the invention.

It is to be understood that these drawings are solely for the purpose of illustrating the concepts of the invention and are not intended as a definition of the limits of the invention. The embodiments shown in the figures herein and described in the accompanying detailed description are to be used as illustrative embodiments and should not be construed as the only manner of practicing the invention. Also, the same reference numerals, possibly supplemented with reference characters where appropriate, have been used to identify similar elements.

FIG. 1 illustrates a flow chart 100 of a process for managing equipment and/or transducers in accordance with the principles of the invention. In this illustrative aspect of the invention, a request is made for specific or designated equipment at block 110, which may include one or more transducers. Hence, the request may be made with regard to specifically-identified equipment or device or a specifically-identified transducer located on a device. Although the invention is now described with regard to a medical device or one or more transducers attached to a medical device, it would be recognized by those skilled in the art that requests for other types of equipment may be similarly made. For example, the present invention may be used to track biopsy guides that are sometimes used in conjunction with the transducers.

The request may be made by a manual request entered by an operator (block 105) or may be made based on a predetermined worklist (block 107), or it may be deduced from operator selections of a study type or procedure. In one embodiment, a predetermined worklist may be used to determine the study type or procedure. For example, a "modality list," which is referred to as DICOM standard Modality Worklist, (see for example, Digital Imaging and Communications in Medicine (DICOM), National Electrical Manufacturers Association, 2003, http://medical.nema.org/dicom/2003.html), which is known in the medical arts as a list of steps or procedures used to diagnose an ailment. may be used to determine when specific equipment is needed. In this case, certain steps or procedures, dependent upon the list, require that a specific piece of equipment, such as an x-ray machine or an ultrasonic device, be available. Hence, the requests may be made automatically as the diagnosis steps are executed and the next step is to be performed. Although not shown, it would be recognized that the request may be performed periodically—e.g., hourly, weekly, monthly—in order to continually monitor the location of equipment. With the information regarding a determined location, including the last time of equipment or transducer location, an operator may, depending upon the latency of the information, manually request an update or proceed to the last recorded location. In another aspect of the invention, the request may be continuously made and the results stored in a data base in order to track the location or movement of the equipment. In this manner, the location of the equipment may be predicted based on its movement. In a more automated manner, the requests may be made dynamically based on the patient worklist to insure that equipment is available when needed, as previously noted.

Figure 2:
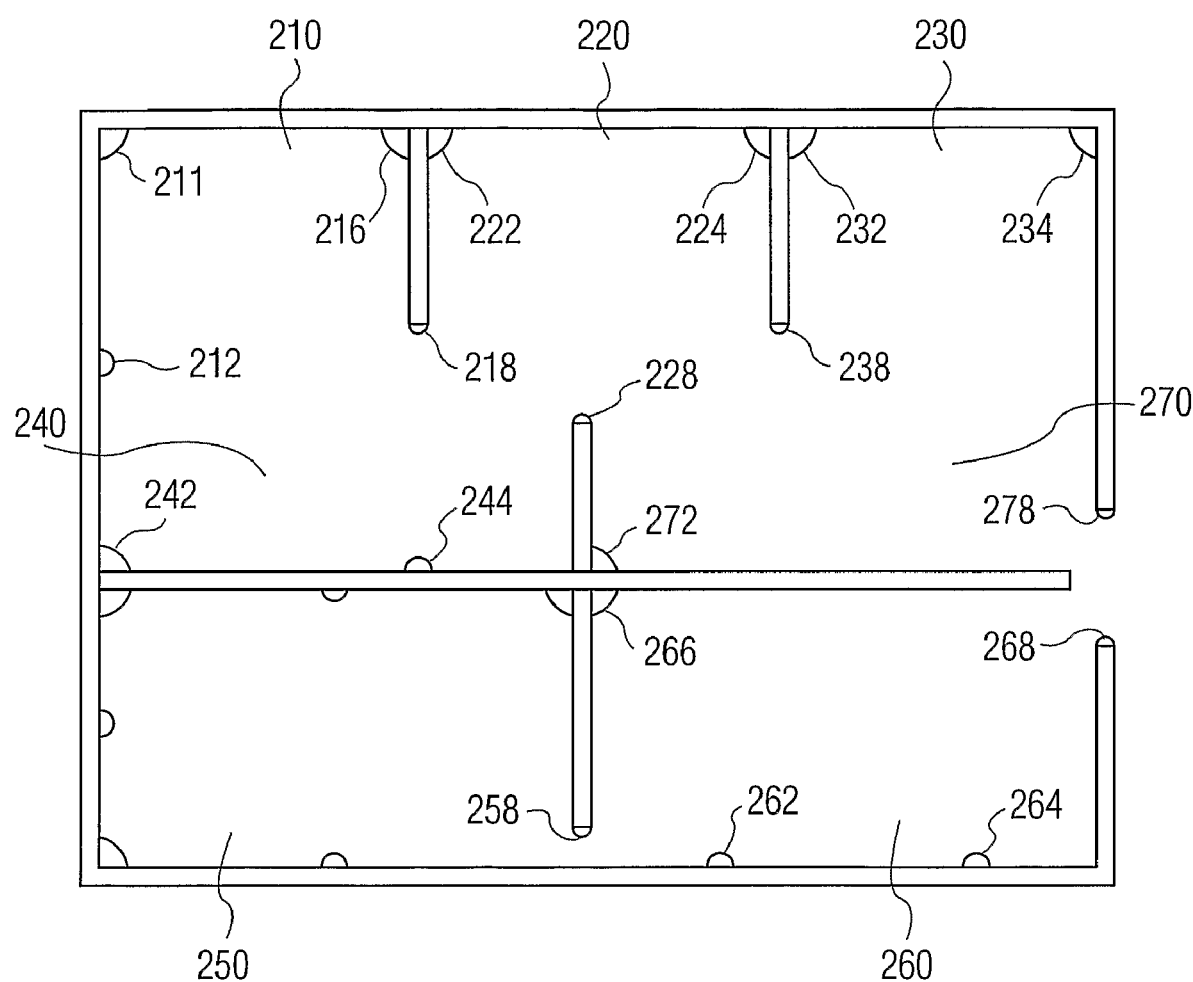
FIG. 2 illustrates an exemplary network for managing equipment/inventory in accordance with the principles of the invention.
Figure 3:
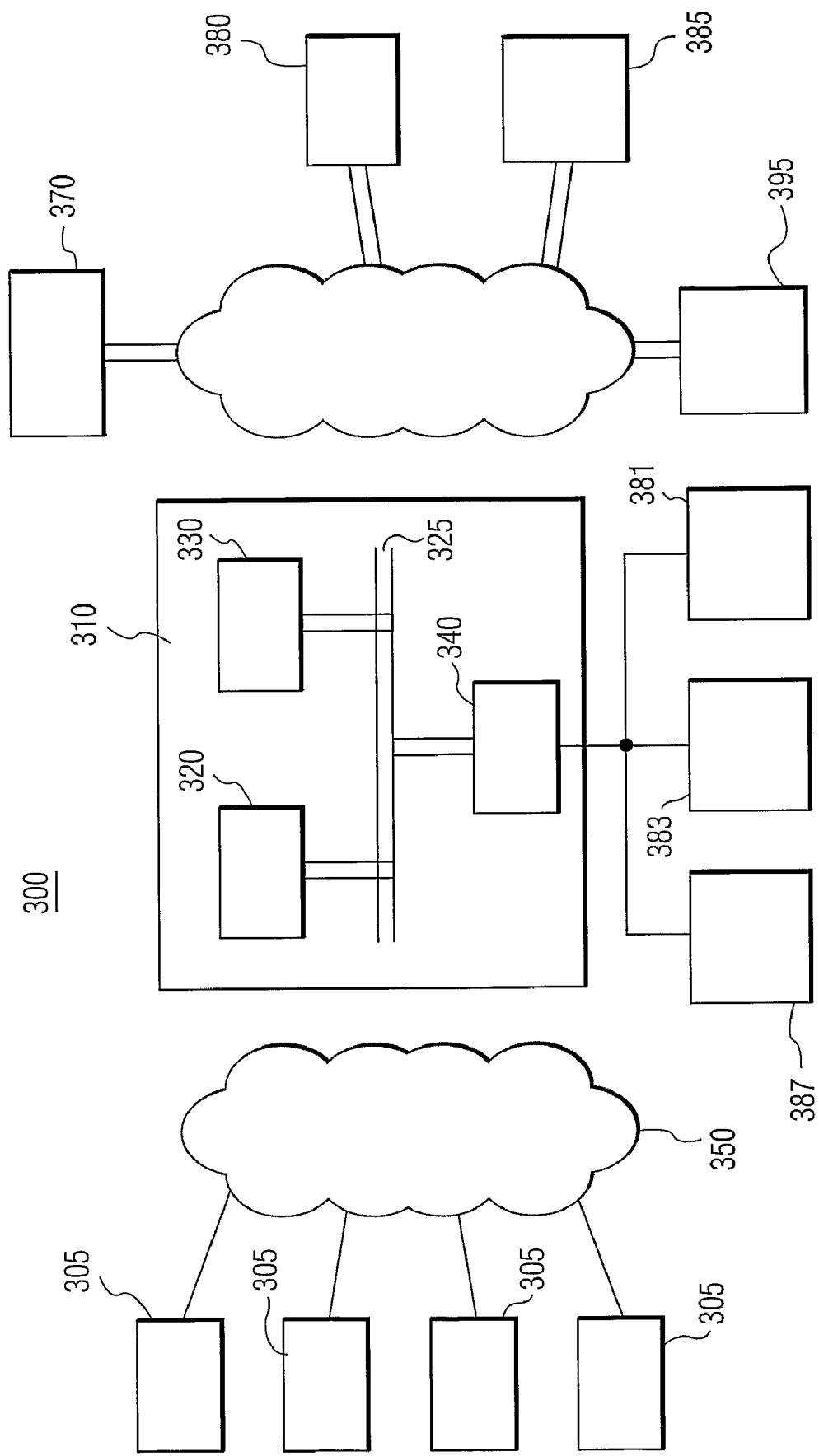
FIG. 3 illustrates a system for managing equipment/inventory in accordance with the principles of the invention.

Returning to FIG. 1, at block 120, a request is transmitted via a network, as it will be more fully described with regard to FIGS. 2 and 3, to search for a desired or requested device and/or transducer. At block 130, a determination is made whether the requested device and/or transducer has responded to the request, e.g., "found." If the answer is in the affirmative, then a determination is made, at block 140, whether the requested device and/or transducer has been "found" or detected on multiple sensors. If the answer is negative, then the sensor "finding" the requested device and/or transducer with the strongest signal strength is identified, at block 150, and the location is displayed at block 160. In this case, the location is displayed based on the single sensor detecting or finding the requested device and/or transducer 160, and, as one skilled in the art would recognize, the location provided by the single sensor provides a general indication of the location.

Returning to the determination at block 140, if the answer is negative, an examination of an "exit database" is made at block 170. At block 180, a determination is made whether the requested device and/or transducer is recorded in the "exit database." If the answer is in the affirmative, then an indication of the exit is displayed at block 185. Otherwise, an indication that the requested device is "not found" is recorded or displayed at block 190.

In another aspect of the invention, when it is determined that the requested device and/or transducer has been detected by multiple sensors, a more precise location of the requested device may be made by correlating the signal strengths of the multiple sensors detecting the requested device. In this aspect of the invention, based on the location of the sensors with respect to one another and the received signal strength at each sensor, the location of the requested device may be more accurately determined. Location determination based on the received signal strength at multiple locations is well-known in the art and need not be discussed in detail herein.

FIG. 2 illustrates an exemplary configuration of sensors 211-278 located in space 200. In this illustrative configuration, sensors 211, 212 and 216, for example, are distributed in a manner to detect the presence of equipment or devices containing transducers in space 210, and sensors 242 and 244 are distributed in a manner to detect the presence of equipment in space 240. Equipment placed in space 210, for example, may be detected primarily by sensors 211, 212 and 216, and, to a lesser extent, by sensors 242 and 244. As noted above, in one aspect of the invention, the location of the desired equipment may be determined by correlating the relative magnitude of the signal strengths received on each sensor. Thus, the more sensors detect a signal from the desired equipment, device or transducer, the more accurate the determination of the equipment location.

The remaining sensors shown are similarly positioned or distributed within the area to detect the presence of equipment in their respective areas and need not be discussed in detail. Although not shown, it would be recognized that each sensor is connected to a network, which may be wired or wireless, and that is used to transmit requests from a central station, not shown, or return detection information to a central station. The central station uses the returned detection information to determine the location of the desired equipment.

Sensors 218, 228, 238, 258, 268 and 278, which may be similar to the sensors distributed throughout the known areas, are specially designated sensors based on their position at locations between spaces. Sensors 218, 228, 238, 258, 268 and 278 are positioned between adjacent areas to determine when equipment transitions from one space to another. In the case when one of the sensors 218-278 detects equipment and/or transducer transition from one area to another, the identified equipment and/or transducer may be included in an exit/entry database list. The exit/entry list may be used, as shown in FIG. 1, when equipment is not found when a request is made.

In one aspect of the invention, at least one RF-ID transponder (tag) is included in a transducer attached to the equipment or to designated components of the equipment. RFID technology is well-known in the art. (See, for example, "*RFID Handbook: Fundamentals and Applications in Contactless Smart Cards and Identification*," Finkenzeller, Chap. 3, John Wiley & Sons, Ltd. ISBN: 0-470-84402-7). In the present invention, the RF-ID tag transponder associated with a transducer provides a response to a transmitted request. Preferably using VHF or UHF RF-ID frequencies, which have a limited sensing/transmitting range—i.e.; in the order of 2-4 meters—sensors 211, 212, and 214, in space 210, for example, may be positioned apart in the order of 4-8 meters.

Each RF-ID tag further includes a unique identification characteristic, for example, a serial number, which is transmitted when a request is made to determine the location of the transducer incorporating the RF-ID tag. The location of the equipment then may be determined by correlating the detection by at least one sensor with the desired RFID tag identification. In one aspect, the location may be approximated as the sensor receiving the highest signal strength. In another aspect, the location may be determined, i.e., refined, based on the signal strength of the received response on a plurality of sensors.

As noted previously, an RF-ID tag may be contained in a transducer associated with equipment and/or associated with components that are incorporated into the equipment. Hence, the desired equipment may include a plurality of transducers, hence, a plurality of RF-ID tags. In this case, a request may be made to locate the desired equipment device and a plurality of responses, one for each associated RF-ID tag incorporated into the equipment, may be made. The location may then be determined or made known by correlating the independently-determined locations of each RF-ID tag or transducer.

FIG. 3 illustrates a system 300 for implementing the principles of the invention as depicted in the exemplary processing shown in FIGS. 1 and 2. In this exemplary system 300, input data is received from sources or devices 305 over network 350 and is processed in accordance with one or more programs, either software or firmware, executed by processing system 310. The results of processing system 310 may then be transmitted over network 370 for viewing on display 380, read/write device 385, reporting device 390 and/or a second processing system 395.

More specifically, processing system 310 includes one or more input/output devices 340 that receive data from the illustrated source devices 305 over network 750 in response to a request to provide source devices 305. The received data is then applied to processor 320, which is in communication with input/output device 340 and memory 330. Input/output devices 340, processor 320 and memory 330 may communicate over a communication medium 325. Communication medium 325 may represent a communication network, e.g., ISA, PCI, PCMCIA bus, one or more internal connections of a circuit, circuit card or other device, as well as portions and combinations of these and other communication media. Processing system 310 and/or processor 320 may be representative of a handheld calculator, special-purpose or general-purpose processing system, desktop computer, laptop computer, palm computer, or personal digital assistant (PDA) device, etc., as well as portions or combinations of these and other devices that can perform the operations illustrated. This processing system may be embedded in an ultrasound imaging system, or other related medical equipment, or may be in stand-alone equipment having a network connection.

Processor 320 may be a central processing unit (CPU) or dedicated hardware/software, such as a PAL, ASIC, FGPA, operable to execute a computer instruction code or a combination of code and logical operations. Memory 330 may be any semiconductor memory such as a ROM, PROM, EEPROM and/or RAM. In one embodiment, processor 320 may include a code which, when executed, performs the operations illustrated herein. The code may be contained in memory 330; may be read or downloaded from a memory medium such as a CD-ROM or floppy disk, represented as 383; may be provided by a manual input device 381, such as a keyboard or a keypad entry; or may be read from a magnetic or optical medium 387 when needed. Information items provided by input devices 381, 383, 387 may be accessible to processor 320 through input/output device 340, as shown. Further, the data received by input/output device 340 may be immediately accessible by processor 320 or may be stored in memory 330. Processor 320 may further provide the results of the processing to display 380, read/write device 385, recording device 390 or a second processing unit 395.

As one skilled in the art would recognize, the term processor, processing system, computer or computer system may represent one or more processing units in communication with one or more memory units and other devices, e.g., peripherals, connected electronically to and communicating with at least one processing unit. Furthermore, the devices illustrated may be electronically connected to the one or more processing units via internal buses, e.g., serial, parallel, ISA bus, microchannel bus, PCI bus, PCMCIA bus, USB, etc., or one or more internal connections of a circuit, circuit card or other device, as well as portions and combinations of these and other communication media, or an external network, e.g., the Internet and Intranet. In other embodiments, hardware circuitry may be used in place of, or in combination with, software instructions to implement the invention. For example, the elements illustrated herein also may be implemented as discrete hardware elements or may be integrated into a single unit.

As would be understood, the operations illustrated may be performed sequentially or in parallel using different processors to determine specific values. Processing system 310 may also be in two-way communication with each of the sources 305. Processing system 310 may further receive or transmit data over one or more network connections from a server or servers over, for example, a global computer communications network such as the Internet, Intranet, a wide area network (WAN), a metropolitan area network (MAN), a local area network (LAN), a terrestrial broadcast system, a cable network, a satellite network, a wireless network, or a telephone network (POTS), as well as portions or combinations of these and other types of networks. As it will be appreciated, networks 350 and 370 may be also internal networks or one or more internal connections of a circuit, circuit card or other device, as well as portions and combinations of these and other communication media or an external network, e.g., the Internet and Intranet.

In another aspect of the invention, the RF-ID tags may also include a transponder that allows the RF-ID tag to receive information from a location system, such as a Global Positioning Satellite system. In this aspect of the system, the RF-ID tag may provide its location based on the information provided from the location system. Hence, in this aspect of the invention, in addition to providing information regarding the unique identification, the information provided may also include its location. The central computer system may then use the location received as the equipment location.

While there has been shown, described, and noted fundamental novel features of the present invention as applied to preferred embodiments thereof, it will be understood that various omissions and substitutions and changes in the apparatus described, in the form and details of the devices disclosed and, in their operation, may be made by those skilled in the art without departing from the spirit of the present invention. It is expressly intended that all combinations of those elements that perform substantially the same function in substantially the same way to achieve the same results are within the scope of the invention. Substitutions of elements from one described embodiment to another are also fully intended and contemplated.

The invention claimed is:

1. An apparatus for determining a location of a transducer within one of a plurality of known areas, said transducer having at least one uniquely identifiable characteristic, said apparatus comprising:
   a plurality of first sensors distributed within said plurality of known areas;
   a plurality of second sensors located between adjacent areas of the plurality of known areas; and
   a processor in communication with a memory for:
      requesting information for locating a first transducer,
      receiving the information from the plurality of first and second sensors, said information including said uniquely identifiable characteristic and a signal strength of the first transducer,
      associating said received information based on said transducer identification, and
      determining a known area of said first transducer location by correlating a relative magnitude of the signal strength received from the first transducer on each of said first and second sensors.

2. The apparatus as recited in claim 1, further comprising a first database for storing said determined transducer location.

3. The apparatus as recited in claim 2, wherein a plurality of transducer locations is collected in said first database over a known period of time.

4. The apparatus as recited in claim 3, a transducer location is predicted based on said plurality of transducer locations stored in said first database.

5. The apparatus as recited in claim 1, further comprising a database, wherein a transition of said transducer from one area to an adjacent area is determined based on a signal strength received by at least one of said second sensors, wherein said transducer transition is stored in the database.

6. The apparatus as recited in claim 1, wherein a request signal including at least one transducer identification is transmitted.

7. The apparatus as recited in claim 6, wherein said request signal is transmitted upon receipt of a command.

8. The apparatus as recited in claim 6, wherein said request signal is transmitted periodically.

9. The apparatus as recited in claim 1, further comprising an input/output device in communication with said processor for receiving information from said first and second sensors.

10. The apparatus as recited in claim 1, further comprising code stored in said memory for executing on said processor.

11. The apparatus as recited in claim 1, wherein said transducer includes an RFID transponder.

12. The apparatus as recited in claim 11, wherein said RFID transponders operate in a frequency range selected from the group consisting of: VHF and UHF.

13. The apparatus as recited in claim 11, wherein said RFID transponder includes a unique identification.

14. A method for determining a location of at least one transducer having at least one uniquely identifiable characteristic, the at least one transducer is located within one of a plurality of known areas, the areas including first sensors distributed within said plurality of known areas and second sensors located between adjacent areas of said plurality of known areas, said method comprising acts of:
  requesting information for locating a first transducer,
  receiving the information from the plurality of first and second sensors, said information including said uniquely identifiable characteristic and signal strength of the first transducer;
  associating said received information based on said identification characteristic; and
  determining a known area of said first transducer location by correlating a relative magnitude of the signal strength received from the first transducer on each of said first and second sensors.

15. The method as recited in claim 14, further comprising an act of storing said location in a first database.

16. The method as recited in claim 15, further comprising an act of collecting a plurality of locations in said first database over a known period of time.

17. The method as recited in claim 16, further comprising an act of predicting a transducer location based on said plurality of transducer locations stored in said first database.

18. The method as recited in claim 14, further comprising acts of:
  determining a transition of said transducer from one area to an adjacent area based on the information received by at least one of said second sensors; and
  storing said transition in a database.

19. The method as recited in claim 14, further comprising an act of transmitting a request signal including at least one transducer identification.

20. The method as recited in claim 19, wherein said request signal is transmitted upon receipt of a manual command.

21. The method as recited in claim 19, wherein said request signal is transmitted periodically.

22. A computer-readable medium comprising a program of instructions for executing a method for determining a location of at least one transducer having at least one uniquely identifiable characteristic, wherein the at least one transducer is located within one of a plurality of known areas, the areas including first sensors distributed within said plurality of known areas and second sensors located between adjacent areas of said plurality of known areas, said method comprising acts of:
  requesting information for locating a first transducer,
  receiving the information from the plurality of first and second sensors, said information including said unique identification characteristic and signal strength of the first transducer;
  associating said received information based on said transducer identification; and
  determining a known area of the first transducer location by correlating a relative magnitude of the signal strength received from the first transducer on each of said first and second sensors.

23. The computer-readable medium as recited in claim 22, further comprising an act of determining said transducer location based on a signal strength received by a plurality of said first sensors within said associated area.

24. The computer-readable medium as recited in claim 22, further comprising an act of storing said transducer location in a first database.

25. The computer-readable medium as recited in claim 24, further comprising an act of collecting a plurality of transducer locations in said first database over a known period of time.

26. The computer-readable medium as recited in claim 25, further comprising an act of predicting said transducer location based on said plurality of transducer locations stored in said first database.

27. The computer-readable medium as recited in claim 22, further comprising acts of:
  determining a transition of said transducer from one area to an adjacent area based on a signal strength received by at least one of said second sensors; and
  storing said transducer transition in a database.

28. The computer-readable medium as recited in claim 22, further comprising an act of transmitting a request signal, said request signal including at least one transducer identification.

29. The computer-readable medium as recited in claim 28, wherein said request signal is transmitted upon receipt of a command.

30. The computer-readable medium as recited in claim 28, wherein said request signal is transmitted periodically.

31. The computer-readable medium as recited in claim 22, wherein the information said location is selected from the group consisting of: a signal strength or a location.

* * * * *